(12) United States Patent
Howard, Jr. et al.

(10) Patent No.: US 9,073,125 B2
(45) Date of Patent: Jul. 7, 2015

(54) LAMINATES OF CHITOSAN FILMS

(75) Inventors: Edward George Howard, Jr., Hockessin, DE (US); Ralph Birchard Lloyd, Fayetteville, NC (US); Ronald James McKinney, Wilmington, DE (US); Bryan Benedict Sauer, Boothwyn, PA (US); Mark Gary Weinberg, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 1489 days.

(21) Appl. No.: 11/593,958

(22) Filed: Nov. 7, 2006

(65) Prior Publication Data

US 2007/0196404 A1    Aug. 23, 2007

Related U.S. Application Data

(60) Provisional application No. 60/734,326, filed on Nov. 7, 2005.

(51) Int. Cl.
| | |
|---|---|
| *B23B 27/12* | (2006.01) |
| *A61K 31/722* | (2006.01) |
| *A62D 5/00* | (2006.01) |
| *B32B 9/00* | (2006.01) |
| *B32B 9/02* | (2006.01) |
| *C08J 5/18* | (2006.01) |

(52) U.S. Cl.
CPC .......... *B23B 27/12* (2013.01); *B32B 2307/714* (2013.01); *A61K 31/722* (2013.01); *A62D 5/00* (2013.01); *B32B 9/00* (2013.01); *B32B 9/02* (2013.01); *B32B 2307/7145* (2013.01); *B32B 2307/724* (2013.01); *C08J 5/18* (2013.01); *C08J 2305/08* (2013.01)

(58) Field of Classification Search
CPC ...... B32B 9/00; B32B 9/02; B32B 2307/714; B32B 2307/724; C08J 2305/08
USPC ............................ 442/59; 514/55; 2/457, 257
See application file for complete search history.

(56) References Cited

U.S. PATENT DOCUMENTS

| | | | |
|---|---|---|---|
| 2,040,880 | A | 5/1936 | Rigby |
| 5,015,293 | A | 5/1991 | Mayer et al. |
| 5,762,643 | A * | 6/1998 | Ray et al. ...................... 604/383 |
| 6,197,322 | B1 * | 3/2001 | Dutkiewicz et al. .......... 424/412 |
| 6,399,853 | B1 * | 6/2002 | Roe et al. ...................... 604/362 |
| 6,746,762 | B1 * | 6/2004 | Hosoda et al. ................. 428/332 |
| 6,982,231 | B1 * | 1/2006 | Uitenbroek et al. .......... 442/394 |
| 2003/0023216 | A1 * | 1/2003 | Carlucci et al. ............... 604/375 |
| 2004/0116022 | A1 * | 6/2004 | Langley et al. ............... 442/289 |
| 2005/0181024 | A1 | 8/2005 | Sabesan |

OTHER PUBLICATIONS

Truong, Q., "20: Chemical and biological protection", Textiles for Protection, Oct. 2005, Woodhead Publishing Limited, pp. 557-594.*
Muzzarelli et al., "N-(Carboxymethylidene)chitosans and N-(Carboxymethyl)-Chitosans: Novel Chelating Polyampholytes Obtained from Chitosan Glyoxylate", Carbohydrate Research, 107 (1982), pp. 199-214.

(Continued)

*Primary Examiner* — Peter Y Choi

(57) ABSTRACT

Chitosan films and laminates made from the films are provided. The films and laminates can be used to make a variety of finished articles that can be used to provide protection from hazardous chemical and biological agents.

7 Claims, 1 Drawing Sheet

(56) References Cited

OTHER PUBLICATIONS

Muzzarelli et al., "Aspartate Glucan, Glycine Glucan, and Serine Glucan for the Removal of Cobalt and Copper from Solutions and Brines", Biotechnology and Bioengineering, vol. XXVII, (1985), pp. 1115-1121.

Cohen et al., "Coating Processes", Kirk-Othmer Encyclopedia of Chemical Technology, John Wiley & Sons, 5$^{th}$ Edition, vol. 7, (2004), pp. 1-35.

Knaul et al., "Methods for Improving the Mechanical Properties of Chitosan Fibers", Advances in Chiton Science, vol. 3, (1998), pp. 399-406.

Bodnar et al., "Nanoparticles from Chitosan", Polymer Preprints, (2004), 45(2), pp. 307-308.

Huang et al., "A review on polymer nanofibers by electrospinning and their applications in nanocomposites", Composites Science and Technology 63, (2003), pp. 2223-2253.

Donaldson et al., "A Durable Flame Retardant Finish for Cotton Based on THPC and UREA", J. Coated Fabrics, vol. 3(2974), pp. 250-256.

* cited by examiner

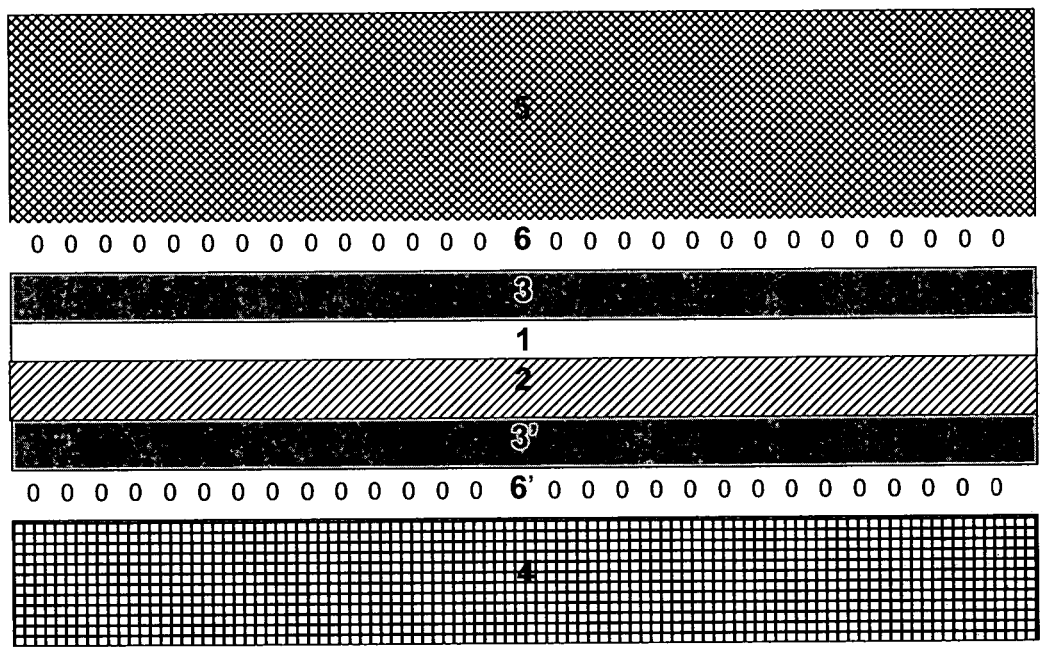

LAMINATES OF CHITOSAN FILMS

This application claims the benefit of U.S. Provisional Application No. 60/734,326, filed Nov. 7, 2005, which is incorporated in its entirety as a part hereof for all purposes.

TECHNICAL FIELD

The present invention relates to laminates prepared in part from continuous chitosan films. In various embodiments, the laminates are useful for fabrication as a protective article and are preferably substantially impermeable to hazardous chemical and biological agents, but sufficiently permeable to water vapor that, if worn as protective apparel, it is both protective and comfortable to wear.

BACKGROUND

There is a growing need for structures that provide personal protection against toxic chemical and biological agents. It is known to devise structures that are impermeable to toxic chemical vapors and liquids, but, when used as apparel, such structures are typically also hot, heavy and uncomfortable to wear.

The degree of comfort offered by apparel worn as a protective suit is significantly affected by the amount of water vapor that can permeate through the fabric from which the suit is made. The human body continuously perspires water as a method for controlling body temperature. When a protective fabric hinders the loss of water vapor from the body, the transpirational cooling process is hindered, which leads to personal discomfort. When a protective suit allows little or no loss of water vapor, extreme heat stress or heat stroke can result in a short period of time. Hence, it is desirable that, in addition to offering the highest levels of protection against toxic chemicals and liquids, a practical chemical and biological protective suit should have high water vapor transmission rates. It is also desirable that the appropriate protective structure be light in weight and offer the same high level of protection over a long period of time.

In co-pending U.S. patent application Ser. No. 10/883,105, ballistic fabric articles and protective gear comprising aramid, polybenzazole or high performance polyethylene fibers are treated with a solution containing a chitosan agent to render the articles antimicrobial, thereby preventing the development of odor, and fungal and bacterial growth. The chitosan agent can be applied to the article directly, to the fiber or as a fabric finish.

The present invention provides selectively permeable laminates that contain a continuous chitosan film and that can be used in articles for personal protection, providing improved wearer comfort compared with impermeable articles . . . .

SUMMARY OF THE INVENTION

One aspect of the present invention is a method of inhibiting the permeation of a chemically or biologically harmful agent through a laminate or a structure or item of apparel fabricated therefrom, by including within the laminate a continuous chitosan film.

Another aspect of the present invention is a protective structure comprising a continuous chitosan film. In some embodiments, the structure is a laminate further comprising at least one layer of fabric.

A further aspect of the present invention is a finished article incorporating a laminate that comprises a continuous chitosan film and at least one layer of fabric. Finished articles include items of apparel, shelters, and protective covers.

These and other aspects of the present invention will be apparent to one skilled in the art in view of the following description and the appended claims.

BRIEF DESCRIPTION OF THE DRAWINGS

FIG. 1 is a schematic diagram showing the structure of one type of selectively permeable laminate according to an embodiment of the present invention.

DETAILED DESCRIPTION

In the context of this disclosure, a number of terms shall be utilized.

The term "film" as used herein means a thin but discrete structure that moderates the transport of species in contact with it, such as gas, vapor, aerosol, liquid and/or particulates. A film may be chemically or physically homogeneous or heterogeneous. Films are generally understood to be less than about 0.25 mm thick.

The term "sheet" or "sheeting" as used herein means a film that is at least 0.25 mm thick.

Unless otherwise stated or apparent by the particular context, the term "chitosan" as used herein includes chitosan-based moieties including chitosan itself, chitosan salts, and chitosan derivatives.

The term "chitosan film" as used herein means a film that contains at least one chitosan-based moiety in the amount of at least 50% by weight.

The term "nonporous" as used herein denotes a material or surface that does not allow the passage of air other than by diffusion.

The term "continuous chitosan film" as used herein means a chitosan film having at least one nonporous surface.

The term "permeable" as used herein means allowing liquids or gases to pass or diffuse through.

The term "selectively permeable" as used herein means allowing passage of certain species but acting as a barrier to others.

The term "laminate" as used herein means a material comprising two or more parallel layers of material that are at least partially bonded to each other.

The term "substrate" as used herein means the material onto which a film is formed from solution.

The term "work device" as used herein denotes a substrate which is used only for film formation and does not subsequently become part of a laminate.

The term "soluble" as used herein denotes a material that forms a visibly transparent solution when mixed with a specified solvent. For example, a water-soluble material forms a transparent solution when mixed with water, while a water-insoluble material does not.

The term "chitosan solution" as used herein indicates that at least one chitosan moiety is dissolved in the indicated solvent. However, materials that are insoluble in the indicated solvent may also be present.

The term "(in)solubilize" as used herein means to render a material (in)soluble in a specified solvent.

The term "harmful to human health" as used herein means causing injury to humans as a consequence of acute or chronic exposure through dermal contact, ingestion, or respiration.

In preferred embodiments, the chitosan films and laminates made therefrom are substantially impermeable to certain biological and/or chemical agents. It is often desirable that the films and laminates be at least 99% impermeable to certain agents, even up to 100% impermeable.

In one embodiment, the present invention provides a protective structure, fabricated from a continuous chitosan film or a selectively permeable laminate containing a continuous chitosan film. "Structure", as used herein with regard to structures fabricated from the continuous chitosan film, includes single layers and multiple layers of continuous chitosan films. Chitosan films can be used to make laminates. The structures can be used in articles and items of apparel that protect against exposure to a chemical or biological agent that is harmful to human health. Specific embodiments include finished articles, including articles of apparel, fabricated from a continuous chitosan film or a selectively permeable laminate containing a continuous chitosan film.

In other embodiments, the invention provides methods of inhibiting the permeation of a chemically or biologically harmful agent through a selectively permeable laminate, or through an article or item of apparel fabricated therefrom, by including within the selectively permeable laminate a continuous chitosan film.

In further embodiments the invention provides methods of fabricating a structure that protects against exposure to a chemical or biological agent that is harmful to human health, and methods of fabricating items of apparel, by incorporating into a structure or item of apparel a selectively permeable laminate containing a chitosan film.

Because the laminates are selectively permeable, we have found that a structure fabricated therefrom provides a protective barrier that inhibits the permeation through the laminate, and thus through the structure, of chemical and biological agents that may be harmful to humans while maintaining sufficient water vapor permeability to maintain personal comfort when the laminate is used to fabricate an item of apparel.

The selectively permeable laminates described herein contain a continuous chitosan film. In one embodiment, the laminate is a chitosan film deposited from solution onto a substrate. In another embodiment, the laminate is a chitosan film adhered to a layer, for example, polyurethane film by thermal bonding. In another embodiment, a continuous chitosan film or a chitosan film cast onto a substrate, or a chitosan film thermally bonded to another layer is bonded to one or more layers of fabric, by adhesive. The adhesive can be in the form of stripes or, preferably, dots, to provide a discontinuous layer of adhesive, in order not to block passage of gases and/or liquids through the selectively permeable laminate. FIG. 1 illustrates one embodiment of a selectively permeable laminate that could be used in, for example, an article of apparel. In the embodiment shown, the laminate contains the following elements a continuous chitosan film (1); a substrate to which the continuous chitosan film is adhered (2); additional layers (3, 3'); an inner liner (4); an outer shell (5) and adhesive (6, 6'). However, not all embodiments of the selectively permeable laminates contain all of the elements shown in FIG. 1.

Continuous Chitosan Film

Chitosan is the commonly used name for poly-[1-4]-β-D-glucosamine. It is commercially available and is chemically derived from chitin, which is a poly-[1-4]-β-N-acetyl-D-glucosamine that, in turn, is derived from the cell walls of fungi, the shells of insects and, especially, crustaceans. In the preparation from chitin, acetyl groups are removed, and, in the chitosan used herein, the degree of deacetylation is at least about 60%, and is preferably at least about 85%. As the degree of deacetylation increases, it becomes easier to dissolve chitosan itself in acidic media.

Suitable chitosan-based moieties include chitosan itself, chitosan salts, and chitosan derivatives. Representative examples of chitosan derivatives suitable for use in this invention include N- and O-carboxyalkyl chitosan. The number average molecular weight ($M_n$) in aqueous solution of the chitosan used herein is at least about 10,000.

A chitosan film may be cast from solution. If it is desired to cast a chitosan film from an aqueous solution, however, the chitosan is first solubilized, since chitosan itself is not soluble in water. Preferably, solubility is obtained by adding the chitosan to a dilute solution of a water-soluble acid. This allows the chitosan to react with the acid to form a water-soluble salt, herein referred to as a "chitosan salt" or "chitosan as the (acid anion) thereof", for example "chitosan as the acetate thereof" if acetic acid was used. Chitosan derivatives such as N- and O-carboxyalkyl chitosan that are water-soluble can be used directly in water without the addition of acid.

The acid used to solubilize the chitosan may be inorganic or organic. Examples of suitable inorganic acids include without limitation hydrochloric acid, sulfamic acid, hot sulfuric acid, phosphoric acid and nitric acid. Suitable organic acids may be selected from the group consisting of water-soluble mono-, di- and polycarboxylic acids. Examples include without limitation formic acid, acetic acid, pimellic acid, adipic acid, o-phthalic acid, and halogenated organic acids. Other suitable acids are disclosed in U.S. Pat. No. 2,040,880. Mixtures of acids may also be used. Volatile acids, that is, those with a boiling point less than about 200° C., are preferred.

The amount of acid used to solubilize the chitosan can be chosen to control the viscosity. If too little acid is added, the resulting solution may be too viscous to cast a thin film and/or to be filtered. The desired amount of acid used will also depend on the desired chitosan concentration in the final solution. It will depend as well on the molecular weight and degree of deacetylation of the starting chitosan, since those properties determine the molar concentration of amino groups (—$NH_2$) available to react with the acid. Preferably, about one acid equivalent is added per mole of chitosan amino group (—$NH_2$).

The appropriate concentration of chitosan in the final solution will vary depending on how the solution is to be applied, and also on the molecular weight of the chitosan, as a lower concentration may be desired for a relatively high molecular weight chitosan. Different application methods work best with solutions of different viscosities, but typically, the solution will contain from about 0.1 to about 15 wt % chitosan, based on the total combined weight of the solution and the chitosan.

The chitosan solution from which the film is prepared may include organic polymers, including without limitation, natural polymers such as starch or cellulose, and synthetic polymers such as polyurethanes, polyamides, and polyesters. Such polymers may be soluble or insoluble in the chitosan solution. For example, a polyamide may be dissolved in a solution of chitosan and formic acid, while a polyurethane suspension in water would remain a suspension when added to a chitosan/acetic acid solution.

The chitosan solution from which the film is prepared may include inorganic fillers, including without limitation, glass spheres, glass bubbles, clays (e.g., sepiolite, attapulgite, and montmorillonite) and the like. Small amounts of such fillers, preferably less than 10 wt %, could be used to increase thermal stability, modulus, and barrier properties of the chitosan film where this is desirable.

The chitosan solution from which the film is prepared may include additives such as flame retardants, plasticizers, stabilizers, tougheners, and the like, to enhance various properties of the chitosan film such as strength, flexibility, fire resistance and dimensional stability. For example, flexibility of the film when wet can be enhanced by addition of ketoacids such as glyoxylic acid and levulinic acid, which react with chitosan to form N-(carboxymethylidene) chitosans (see, e.g., R. A. A. Muzzarelli et al., Carbohydrate Research (1982), 107, 199-214; R. A. A. Muzzarelli et al., Biotechnology and Bioengineering (1985), 27, 1115-1121). N-(carboxymethylidene) chitosans can be insolubilized by heat-treating and are physically flexible in the presence of moisture. In other examples, film insolubility can be obtained by adding sugars such as glucose and fructose to the chitosan solution. Additives to a chitosan solution may be soluble in the solution, or they may be present as dispersed insoluble material. Adding sugars and di- or multi-functional acids can reduce the thermal requirements for rendering the chitosan insoluble. With these additives, annealing temperatures of about 100° C.-120° C. for about 1 to 10 minutes cause insolubility. The additives are present at less than 50% by weight, based on the weight of chitosan plus additives.

A chitosan film may be prepared by casting a chitosan solution directly onto a substrate that will be incorporated along with the film into a laminate. Alternatively, the chitosan solution may be cast onto a work device such as a smooth surface, such as glass or a polymer film (for example, polyester film). If the film is cast onto a work device, the film is then dried, detached and then incorporated into a laminate in a separate step.

The solution may be applied to a substrate by any of a variety of methods known in the art. For a small scale process, such as a laboratory test sample, the solution is typically applied using a doctor knife. Methods available to coat surfaces which are planar and have irregular surfaces include without limitation spray coating, dip coating, and spin coating. In a commercial process, the solution could be applied to, e.g., traveling web using methods that include without limitation reverse roll, wire-wound or Mayer rod, direct and offset gravure, slot die, blade, hot melt, curtain, knife over roll, extrusion, air knife, spray, rotary screen, multilayer slide, coextrusion, meniscus, comma and microgravure coating. These and other suitable methods are described by Cohen and Gutoff in "Coating Processes" in the *Kirk-Othmer Encyclopedia of Chemical Technology* [John Wiley & Sons, 5$^{th}$ edition (2004), Volume 7, Pages 1-35]. The method chosen will depend on several factors, such as the rheology of the solution to be applied, the desired wet film thickness, the speed of a substrate that is traveling, and the required coating accuracy as a percent of total thickness.

The applied solution is then dried by any suitable means known in the art such as exposure to a hot air oven, air impingement drying, or radiative (e.g. infrared or microwave) drying (See, generally, Cohen and Gutoff, op. cit.). The result of the drying at this stage is a continuous film. If the chitosan is dissolved in an aqueous solution of a volatile acid, that is, an acid whose boiling point is less than about 200° C., exposure to ambient air may be sufficient for drying, and drying will remove acid as well as water.

If a film at this stage is water-soluble, it can be made water-insoluble by heating; by reacting it with a crosslinking reagent; by treatment with a strong base; or by a combination of two or more of these methods. For example, a films cast from a formic acid solution can be made water-insoluble by heat treatment after the film has been formed and dried, for example, by heating at about 100° to about 260° C. for about 0.1 to about 60 minutes, or more preferably about 100° C. to 180° C. for about 1 to 10 minutes. Heat treatment plus the use of a crosslinking agent could also be used to render the chitosan film insoluble.

The film can also be made insoluble by adding any of a variety of crosslinking agents to a solution before a film is cast therefrom. A crosslinking agent is a reactive additive that creates bonds, i.e. crosslinks, between polymer chains. Examples of crosslinking agents for chitosan include without limitation glutaraldehyde (J. Knaul et al., Advances in Chitin Science (1998), 3 399-406), epichlorohydrin (U.S. Pat. No. 5,015,293), and di-, and tri-carboxylic acids including succinic, malic, tartaric, and citric acids (M. Bodnar, Magdolna et al., Abstracts of Papers, 228th ACS National Meeting, Philadelphia, Pa., United States, Aug. 22-26, 2004 (2004), POLY-179). Diacids such as adipic acid or other multifunctional acids such as levulinic acid, glyoxylic acid or halogenated organic acids, can be used to make the chitosan solution. With these additives, temperatures of about 100° C.-120° C. for about 1 to 10 minutes can cause insolubility. Crosslinking agents may also be applied to the film after it is dried.

The film can also be made water-insoluble by contacting the film with a base and then washing, which converts the film from the chitosan salt form to free chitosan. If the film to be treated with base is attached to a substrate, the composition and concentration of the base will be influenced by the nature of the substrate (e.g., its reactivity toward base) and processing conditions (e.g., temperature and contact time, continuous versus batch process). Typically, the base is a 1% to 10% by weight aqueous solution of sodium hydroxide, and typical contact times are 30 seconds to 3 hours at ambient temperature. Heat treatment plus contact with base could also be used to render the film insoluble.

Substrate Materials

Although a free-standing chitosan film can be incorporated into a protective article, it can also be adhered to a substrate. Referring to FIG. 1, a chitosan film 1 may be prepared by casting a chitosan solution directly onto a substrate 2 that will be incorporated along with the film into a laminate. It can also be cast on a work surface like PET film and coated with an additional layer or layers before or after the work surface is removed and discarded. In certain cases, the substrate onto which a chitosan film may be prepared may itself be a continuous sheet or film, provided that the permeability of the substrate to water vapor under use conditions is adequate for the particular end use. For example, a garment would require much higher water vapor permeability than a tent or tarpaulin.

A suitable substrate will have at least one surface that is smooth, i.e., essentially without protrusions above the plane of the substrate that are higher than the desired thickness of the coating of chitosan that will be transformed into the film. Thus, a smoother substrate surface is required when the desired thickness of the coating of chitosan is 25 microns than when it is 100 microns.

A suitable substrate may be, for example, a film, a sheet whose permeability to water vapor under use conditions is adequate for the particular end use, a microporous membrane (i.e., one in which the typical pore size is about 0.1 to 10 micrometers in diameter), or an article prepared from any of the foregoing. It is preferred that the substrate surface that will be in contact with the chitosan film be both smooth and nonporous. Suitable substrate materials include polar polymer films, including elastomers, glassy polymers, and semi-crystalline materials. A polar polymer has both dispersion and dipole-dipole forces, while a non-polar polymer has only dispersive attractive forces. Polar polymers generally contain a substantial fraction of oxygen and nitrogen containing groups, while non polar polymers contain a substantial fraction of hydrocarbon or fluorocarbon with minimal oxygen and nitrogen containing groups.

Examples of suitable substrate materials include without limitation Nafion® perfluorosulfonic acid tetrafluoroethylene copolymer (available from E. I. du Pont de Nemours and Company, Wilmington, Del., USA), polyurethanes (e.g., polyurethane films available from Omniflex Co., Greenfield, Mass., USA), polyether block polyamide copolymers (e.g., Pebax® polyether block amides available from Arkema, Paris, France), polyether block polyester copolymers, sulfonated styrene-polyolefin di- and tri-block copolymers, and polyvinyl alcohol homopolymers and copolymers.

Additional Layers

The protective laminates described herein comprise a continuous chitosan film and at least one layer of fabric. As appropriate, additional layers (for example, a second fabric layer or a microporous membrane) can be used in a laminate with the objective of (a) creating a composite structure that protects the chitosan film from an environment that may degrade its performance, and/or (b) creating a laminate, and potentially thus a composite structure thereof, that has features in addition to those offered only by the chitosan film and the at least one fabric layer, and/or (c) improving the performance of the final structure. For example, additional films or microporous membranes may be applied to the outer surfaces of the chitosan film and, where present, the substrate, as shown in FIG. 1 (3, 3') by coating, thermal lamination, and other means known in the art, to protect the chitosan and substrate films from dust and liquids or physical damage. One or more layers of ballistic fabrics can be used to absorb the impact of a projectile and protect the wearer from harm.

In many end uses, particularly apparel, the continuous chitosan film (and its associated substrate, where present) is incorporated into a structure that includes an outer layer of material (an "outer shell," 5 in FIG. 1) which is exposed to the environment and/or an inner liner 4.

The outer and inner materials may each be chosen for functional reasons such as ruggedness, ballistic resistance, and resistance to abrasion or tearing, as well as to impart a comfortable feel and a fashionable appearance to apparel. Colored and patterned materials may also be used as outer layers to introduce camouflage features in military applications. The outer shell and inner liner materials are typically fabric or microporous membranes.

Fabrics may be wovens or nonwovens (e.g., nonwoven sheet structures created by spun bonded/melt blown processes or by electrospinning as described in, e.g., Z.-M. Huang et al., Composites Science and Technology (2003), 63, 2223-2253). Fabrics may be prepared from any synthetic or natural fiber appropriate for the specific end use in mind. Preferred fabrics may be prepared from aramids, nylons, polyesters, cotton, and blends comprising any of these, such as, but not limited to blends of nylon and cotton fibers ("NYCO"). The term "nylon" as used herein refers to polyamides other than aramids. An aramid is an aromatic polyamide, wherein at least 85% of the amide (—CONH—) linkages are attached directly to two aromatic rings. Flame retardant fibers, including aramids (preferably up to 40%) may be blended with an aramid to impact fabric thermal performance and comfort. A suitable aramid may be in the form of a copolymer that may have as much as 10 percent of other diamine(s) substituted for the diamine of the aramid or as much as 10 percent of other diacid chloride(s) substituted for the diacid chloride of the aramid. A p-aramid would be preferred in a fabric as used in this invention, and poly(p-phenylene terephthalamide) (PPD-T) is the preferred p-aramid. M-aramids may also find use in the present invention, and poly(m-phenylene isophthalamide) (MPD-I) is the preferred m-aramid. P-aramid and m-aramid fibers and yarns particularly suitable for use in the present invention are those sold respectively under the trademarks Kevlar® and Nomex® (E. I. du Pont de Nemours and Company, Wilmington Del., USA), and Teijinconex®, Twaron® and Technora® (Teijin Ltd., Osaka, Japan), and equivalent products offered by others. Typically, the aramid fabric would be used in the outer shell, and the inner liner would more likely contain fabric such as polyester, nylon, cotton, or blends thereof, though m-aramids may be utilized as part of the inner liner as well to improve fire resistance Films and microporous membranes may be prepared from any synthetic or natural material appropriate for the specific end use in mind. Examples of films and microporous membranes that can be used as a component of inner liners or outer shells include without limitation expanded poly(tetrafluoroethylene) membranes such as those sold under the trademark GORE-TEX® (W. L. Gore & Associates, Inc., Newark, Del., USA); hydrophobic polyurethane microporous membranes (see, e.g., S. Brzeziński et al., Fibres & Textiles in Eastern Europe, January/December 2005, 13(6), 53-58); microporous (poly)propylene available from, e.g., 3M (St. Paul, Minn., USA); thin films of thermoplastic polyurethane such as those sold under the trademark Transport® Brand Film by Omniflex (Greenfield, Mass., USA); Pebax® polyether block amide by Arkema (Paris, France); and DuPont™ Active Layer, a polyester film available from E. I. du Pont de Nemours and Company (Wilmington, Del., USA).

Fabrication

The selectively permeable laminates described herein can be assembled using any of the any of the sewing, stitching, stapling or adhering operations, such as thermally pressing, known in the art.

Referring to FIG. 1, the layers to be assembled include the chitosan film 1 and at least one other layer. For example, if the chitosan film is cast on a work device, the film is then dried and detached as a free-standing film. Other layers could be added either before or after detachment from the work device. It may then be attached to another layer (for example, substrate, outer shell, inner liner) using an adhesive such as a polyurethane-based adhesive. The adhesive may be present as a continuous layer, an array of adhesive dots, or in a number of alternative patterns such as lines or curves. The adhesive may be applied in a variety of ways including spraying or gravure roll.

To fabricate a structure or other article from a laminate disclosed herein, such as an item of apparel, the laminate may be sandwiched between (additional) woven fabrics. Bonding between the film structure and the fabrics may be continuous or semicontinuous, for example, with adhesive dots or films. Alternatively, the bonding may be discontinuous, for example by sewing the edges together, an arrangement often referred to as a "hung liner". Other means of discontinuous bonding may include the use of Velcro® strips or zippers.

Uses

The laminate, as well as the continuous chitosan film itself, is selectively permeable, having a Moisture Vapor Transport Rate ("MVTR") of at least 2 kg/m$^2$/24 h, while the transport rate of materials harmful to human health is low enough to prevent the occurrence of injury, illness or death. The specific transport rate needed will necessarily depend on the specific harmful material; for example, NFPA 1994, 2006 Revision requires <4.0 μg/cm$^2$ one hour cumulative permeation for mustard and <1.25 μg/cm$^2$ for Soman, both of which requirements are met by the laminates and the continuous chitosan film it contains. Consequently, the laminates, as well as the continuous chitosan film itself, can be used for the fabrication of, or as a component in, a variety of articles of manufacture, including articles of protective apparel, especially for clothing, garments or other items intended to protect the wearer or user against harm or injury as caused by exposure to toxic chemical and/or biological agents, including without limitation those agents potentially used in a warfighter environment and materials identified as "Toxic Industrial Chemicals" (TICs) or "Toxic Industrial Materials" (TIMs); see, for example, *Guide for the Selection of Chemical and Biological Decontamination Equipment for Emergency First Responders, NIJ Guide* 103-00, Volume I, published by the National Institute of Justice, U.S. Department of Justice (October 2001), herein incorporated by reference. A few examples of TICs are phosgene, chlorine, parathion, and acrylonitrile. Permeability of the laminate or a layer in the laminate to specific substances may be determined by various methods including, without limitation, those described in ASTM F739-91, "Standard Test Method for Resistance of Protective Clothing Materials to Permeation by Liquids or Gases Under Conditions of Continuous Contact."

In one embodiment, the item of apparel is useful to protect military personnel against dermal exposure to chemical and biological agents potentially encountered in a warfighter environment. Examples of such agents include without limitation nerve agents such as Sarin ("GB," O-isopropyl methylphosphonofluoridate), Soman ("GD," O-Pinacolyl methylphosphonofluoridate), Tabun ("GA," O-Ethyl N,N-dimethylphosphoramidocyanidate), and VX (O-Ethyl S-2-diisopropylaminoethyl methylphosphonothiolate); vesicant agents such as sulfur mustards (e.g., Bis(2-chloroethyl)sulfide and Bis(2-chloroethylthio)methane); Lewisites such as 2-chlorovinyidichloroarsine; nitrogen mustards such as Bis-(2-chloroethyl)ethylamine ("HN1"); tear gases and riot control agents such as Bromobenzyl cyanide ("CA") and Phenylacyl chloride ("CN"); human pathogens such as viruses (e.g., encephalitis viruses, Ebola virus), bacteria (e.g., Rickettsia rickettsii, Bacillus anthracis, Clostridium botulinum), and toxins (e.g., Ricin, Cholera toxins). A human pathogen is a microorganism that causes disease in humans.

In a further embodiment, the item of apparel is useful to protect first responder personnel from known or unknown chemical or biological agents potentially encountered in an emergency response situation. In yet another embodiment, the item is intended to protect cleanup personnel from chemical or biological agents during a hazmat response situation. Examples of hazardous material in addition to those listed above include certain pesticides, particularly organophosphate pesticides.

Such clothing, garments or other items include without limitation coveralls, protective suits, coats, jackets, limited-use protective garments, raingear, ski pants, gloves, socks, boots, shoe and boot covers, trousers, hoods, hats, masks and shirts.

In another embodiment, the laminates can be used to create a protective cover, such as a tarpaulin, or a collective shelter, such as a tent, to protect against chemical and/or biological warfare agents.

Furthermore, the laminates can be used in various medical applications as protection against toxic chemical and/or biological agents. In one embodiment, the laminates could be used to construct items of apparel for health care workers, such as medical or surgical gowns, gloves, slippers, shoe or boot covers, and head coverings.

EXAMPLES

Specific embodiments of the present invention are illustrated in the following examples. The embodiments of the invention on which these examples are based are illustrative only, and do not limit the scope of the appended claims.

The meaning of the abbreviations used in the examples is as follows: "s" means second(s), "min" means minute(s), "h" means hour(s), "kg" means kilogram(s), "g" means gram(s), "mg" means milligram(s), "µg" means microgram(s), "oz" means ounce(s), "yd" means yard(s), "mmol" means millimole(s), "m" means meter(s), "cm" means centimeter(s), "mm" means millimeter(s), "µm" means micrometer(s), "mL" means milliliter(s), "µL" means microliter(s), "M" means molar, "N" means normal, "wt %" means weight percent, "ppm" means parts per million, "MW" means molecular weight, "$M_n$" means number average molecular weight, "$M_w$" means weight average molecular weight, "ND" means not detected, "Pa" means Pascal, "kPa" means kilopascal, "psig" means pounds per square inch gage, "PU" means polyurethane, and "SEC" means size exclusion chromatography. Unless otherwise specified, the water used is distilled or deionized water.

The chitosan materials used in the following Examples were obtained from Aldrich Chemical Company (Milwaukee, Wis., USA), or Primex Ingredients ASA, Norway under the trademark ChitoClear® chitosan, as noted. According to the manufacturer, Primex ChitoClear® TM-656 has a Brookfield viscosity of 26 cP (0.026 Pa·s, 1% chitosan in a 1% aqueous acetic acid solution). The Mn and Mw were determined by SEC to be 33,000 and 78,000, respectively.

Methods

Standard Chitosan Salt Solution Preparation

This method was used to prepare chitosan solutions for the examples unless otherwise noted. A food blender cup is preheated in a boiling water bath, placed on the blender's motor, and charged with 564 g of hot water and 36 g of chitosan (Primex ChitoClear® TM-656) (0.22 mole —$NH_2$). While stirring strongly, 11.5 g (0.25 mole) formic acid is added. The formic acid is of 98% purity and is obtained from Aldrich Chemical Company (Milwaukee, Wis.). The viscosity increases immediately. After three minutes of stirring, the resulting viscous mass is poured into a Pyrex® glass bottle and heated for 1 h in a boiling water bath. Afterward, it is pressure filtered through coarse filter paper. The solution is cleared of bubbles after standing for three days at room temperature.

This procedure is also suitable for the lower molecular weight chitosans obtained from Aldrich Chemical Company and Primex Ingredients ASA (ChitoClear® TM-850-2); however, for higher molecular weight chitosan (Primex ChitoClear® TM-1292), more water is preferred to produce a suitable casting solution.

Standard Glass Plate Preparation

When films are to be cast onto a work device such as a glass plate, it is important that the glass plate surface be clean. The following cleaning procedure was used for the examples, but any thorough cleaning procedure would be suitable. A Pyrex® glass plate is washed with PEX lab soap, rinsed with water, and wiped dry. The plate is then cleaned with methanol and, finally, coated and rubbed with 10 wt % aqueous NaOH solution and allowed to stand for ten minutes. The plate is ready for casting after a final rinse with water and drying with soft paper towels.

Molecular Weight Determination

The molecular weights of the chitosan samples are determined by size exclusion chromatography using a triple-detector aqueous system, consisting of a Waters 2690 separations module, a Wyatt-DAWN DSP multi-angular (18) light scattering detector, a Waters 410 differential refractometer (Waters Corporation, Milford, Mass., USA), and a Viscotek T60-B viscometer (Viscotek, Houston, Tex., USA). Two TSK-GEL GMPW columns (TOSOH Bioscience LLC, TOSOH Corporation, Tokyo, Japan) are used. The mobile phase is an aqueous solution of 0.3M acetic acid with 0.3M sodium acetate at a flow rate of 0.5 mL/min. The samples have been first dissolved for 4 hours in a shaker.

Moisture Vapor Transmission Rate (Mvtr)

This is measured by a method derived from the Inverted Cup method of MVTR measurement [ASTM E 96 Procedure BW, Standard Test Methods for Water Vapor Transmission of Fabrics (ASTM 1999)]. A vessel with an opening on top is charged with water and then the opening is covered first with a moisture vapor permeable (liquid impermeable) layer of expanded-PTFE film ("ePTFE"), and then with the sample for which the MVTR is to be measured, and finally by woven fabric overlayer [NYCO 50:50 nylon/cotton blend, 6.7 oz/yd$^2$ (0.23 kg/m$^2$) or Nomex® fabric, 5.6 oz/yd$^2$ (0.19 kg/m$^2$), both treated with durable water repellant finish]. The three layers are sealed in place, inverted for 30 minutes to condition the layers, weighed to the nearest 0.001 g, and then contacted with a dry stream of nitrogen while inverted. After the specified time, the sample is re-weighed and the MVTR calculated (kg/m$^2$/24 h) by means of the following equation:

$$MVTR=1/[(1/MVTR_{obs})-(1/MVTR_{mb})]$$

where $MVTR_{obs}$ is observed MVTR of the experiment and $MVTR_{mb}$ is the MVTR of the ePTFE moisture barrier (measured separately). The reported values are the average of results from four replicate samples.

Dimethylmethylphosphonate ("DMMP") Permeation

DMMP is used as a relatively non-toxic stimulant for chemical warfare G-class nerve agents. The DMMP permeation for the examples described below was carried out as follows: a vessel with an opening on top was charged with a measured amount of water containing 0.100% propylene glycol as an internal GC standard. If the sample was a film, the opening was covered with the sample film and a woven fabric overlayer [NYCO 50:50 nylon/cotton blend, 6.7 oz/yd$^2$ (0.23 kg/m$^2$) or Nomex®, 5.6oz/yd$^2$ (0.19 kg/m$^2$), both treated with durable water repellant finish] was placed on top of the film, and the layers were sealed in place. If the sample was a laminate that already had a fabric surface, no additional fabric overlayer was used. In both types of samples, the fabric surface was treated with one 2 μL drop of DMMP (2.3 mg). The vessel was placed in a nitrogen-purged box for 17 h and then the DMMP concentration in the water was measured by GC analysis. Results are reported in μg of DMMP measured in the water after 17 h and are the average of five replicate samples. The DMMP was obtained from Aldrich Chemical Company (Milwaukee, Wis.) and was used as received.

Chlorine Permeation.

This was determined as follows: a vessel with an opening on top was charged with a measured amount of water. The opening was covered with the sample film and then a 50:50 nylon/cotton blend woven fabric overlayer (NYCO; treated with durable water repellant finish). The layers were sealed in place and the sample placed in a chamber. The atmosphere of the chamber was displaced with a chlorine/nitrogen mixture (1000 ppm chlorine in nitrogen from Matheson Tri-Gas, Inc., Montgomeryville, Pa., USA), and the sample was maintained in this environment for 1 h under ambient temperature and pressure. The sample was then removed from the chamber and the water in the vessel was analyzed. An ExStik™ Chlorine Meter (Extech Instruments, Waltham, Mass., USA) was used to measure chlorine. Permeation is reported as μg/m$^2$/h.

Mustard and Soman Transmission Rates.

The military TOP-8-2-501 (dual flow method) was used to test 24 hour permeation against sulfur mustard, $S(CH_2CH_2Cl)_2$, and the nerve agent Soman. Alternatively, the NFPA 1994, 2006 revision was utilized to measure 1 hour permeation accumulation for the same two agents.

Examples 1 and 2 illustrate the preparation and transport properties of continuous chitosan film.

Example 1

A mixture of 7.5 g (47 mmol —$NH_2$) chitosan having a Brookfield viscosity (1% solution in 1% acetic acid) of 20-200 cP (0.02-0.2 Pa·s), obtained from Aldrich Chemical Company (Milwaukee, Wis., USA catalog number 44,886-9), 175 g water and 2.3 g (53 mmol) formic acid prepared in a Pyrex® glass bottle was heated in a boiling water bath and rolled repeatedly until solution was effected. The solution was pressure filtered under about 40 psi (276 kPa) through coarse filter paper. The solution was stored for four days to allow bubbles to separate. Calculated chitosan content: 4.3 wt %.

Two films, 1A and 1B, were prepared by casting the solution onto Pyrex® glass plates using a 30-mil (0.76 mm) doctor knife and drying at 100° C. After a few hours at room temperature, one film (1A) was lifted from the glass by raising the edges with a sharp razor blade. The film was soluble in water, hence still in the formate salt form. Measurements using a NYCO overlayer are MVTR=23.7 kg/m$^2$/day; DMMP permeation=6 μg in 17 h.

Before the second film (1B) was removed from the glass plate onto which it had been cast, the film and glass were placed in a bath of 10 wt % sodium hydroxide aqueous solution for one hour. The film detached itself from the glass plate and was insoluble, hence no longer in the soluble formate salt form.

The second film was rinsed with distilled water until the washings were neutral, then floated onto an aluminum foil coated with a release agent (Reynolds brand aluminum foil), carefully lifted from the water, and air dried. Measurements using a NYCO overlayer were MVTR=17.6 kg/m$^2$/24 h; DMMP permeation=1 μg in 17 h.

Example 2

Chitosan (20 g; 120 mmol; Aldrich Chemical Company) was added to a rapidly stirred solution of formic acid (6.6 g; 120 mmol) in water (380 g). The viscous mass in a bottle was shaken and then rolled on a roll mill for 1 h and then pressure filtered through coarse filter paper. Films were cast from the resulting solution with a 20 mil (0.5 mm) doctor knife onto a flat Pyrex glass plate, dried at 90° C. and then treated with 10% NaOH aqueous solution for 20 minutes. The washed and dried film was removed from the glass by raising the edges of the film from the glass with a razor blade, then pulling the film cautiously from the glass. The thickness of the film was about 20 microns. Measurements using a NYCO woven fabric overlayer were MVTR, 20.4 kg/m$^2$/day, DMMP permeation, 0 μg in 17 h and $Cl_2$ transmission, 0.8 μg/cm$^2$/h. Measurements using a Nomex® overlayer were MVTR, 23.8 kg/m$^2$/day, DMMP permeation, 0 μg in 17 h.

Example 3

This example illustrates that a chitosan salt film may be insolubilized by heating.

A filtered chitosan formate solution prepared by the method described above was cast onto a glass plate and dried at 100° C. (Sample 3A). A section of Sample 3A was then heated at 200° C. for 15 min (Sample 3B). Sample 3B was no longer soluble in water or aqueous acid. MVTR and DMMP permeation were not significantly affected by the heat treatment.

|  | MVTR (kg/m$^2$/24 h) | DMMP (μg in 17 h) |
|---|---|---|
| SAMPLE 3A | 21.7 | 0 |
| SAMPLE 3B | 22.2 | 0 |

Examples 4 and 5 show that changing the molecular weight of the chitosan used to make the film does not significantly alter the MVTR and DMMP barrier properties of chitosan film.

Example 4

A 2.4% solution of chitosan (Primex ChitoClear® TM-1292, $M_n$=232,000 and $M_w$=452,000 as determined by SEC) as the formate was prepared according to the method of Example 2, with 10 g chitosan and 2.8 g formic acid). The mixture in a bottle was rolled on a mill until it was uniform. According to the manufacturer, Primex ChitoClear® TM-1292 has a Brookfield viscosity of 3362 cP (3.362 Pa·s, 1% chitosan in a 1% aqueous acetic acid solution).

A film was cast onto a clean glass plate with a 20-mil (0.51 mm) doctor knife. After drying at 100° C., the film was treated with 10% aqueous NaOH solution for 10 minutes. MVTR and DMMP permeation measurements made with a Nomex® overlayer are presented in Table 1.

Example 5

A solution of 10% low molecular weight chitosan (Primex ChitoClear® TM-850-2) was made as the formate salt in water (3.3 g chitosan/0.55 g formic acid). The mixture in a bottle was rolled on a mill until it was uniform. $M_n$ was determined by SEC to be 18,000, and Mw was 44,000. According to the manufacturer, Primex ChitoClear® TM-850-2 has a Brookfield viscosity of 9 cP (0.009 Pa·s, 1% chitosan in a 1% aqueous acetic acid solution). The product was cast onto a clean glass plate with a 20-mil (0.51 mm) doctor knife. After drying at 100° C., the film was treated with 10% NaOH/water for 10 minutes. MVTR and DMMP permeation measurements made with a Nomex® overlayer are presented in Table 1.

TABLE 1

| Example | ChitoClear® grade | Description (Brookfield viscosity) | MVTR (kg/m$^2$/24 h) | DMMP (μg/17 h) |
|---|---|---|---|---|
| 4 | TM-1292 | High MW (3362 cP) | 29.4 | 3 |
| 5 | TM-850-2 | Low MW (9 cP) | 24.4 | 0 |

Example 6

This example demonstrates the effect of acid type and heat treatment on chitosan film performance.

Chitosan films were prepared from aqueous solutions of chitosan and various acids as indicated in Table 2.

Procedure A

To a suspension of 1 g chitosan (Primex ChitoClear® TM-656 Chitosan) in 10 mL H$_2$O was added a molar equivalent (in terms of the chitosan —NH$_2$ groups) of the indicated acid dissolved in 6 mL of hot or cold water. The mixtures were made in 1 oz (30 mL) scintillation vials. The vials were turned on a ball mill until the contents appeared uniform, then stored to allow bubbles to rise from the viscous solutions before casting films. Where heat treatment was carried out, beyond drying at about 95-100° C. the conditions (maximum temperature and time at that temperature) are indicated in Table 2.

Procedure B (Used for 6H)

The same as Procedure A except for 10× quantity.

Procedure C (Used for 6K)

The same as Procedure A except for using 4 g Chitosan, 65 g water and 1.95 g propionic acid.

Permeation measurements with a NYCO overlayer are provided in Table 2.

TABLE 2

| Sample | Procedure | Acid (g) | Maximum Temp/Time (° C./min) | MVTR (kg/m$^2$/24 h) | DMMP (μg in 17 h) |
|---|---|---|---|---|---|
| 6A | A | o-phthalic (0.5) |  | 32.2 | 0 |
| 6B | A | Sulfamic (0.58) |  | 41.7 | 0 |
| 6C | A | Sulfanilic (1.04) |  | 38.5 | 3 |
| 6D | A | Benzoic (0.73) |  | 17.5 | 0 |
|  | A | Benzoic (0.73) | 200/2 |  |  |
| 6E | A | Succinic (0.35) |  | 27.8 | 14 |
| 6F | A | Palmitic, (1.0) |  | 26.3 | 0 |
| 6G | A | Glutamic |  | 27.0 | 0 |
| 6H | B | Adipic, (4.4) |  | 27.0 | 0 |
| 6I | A | Chloroacetic, (0.59) | 180/0.33 | 27.8 | 7 |
| 6J | A | Formic, (0.24) plus 5-bromovaleric, (0.24) |  | 12.8 | 11 |
| 6K | C | Propionic |  | 33.3 | 0 |
|  |  | Propionic | 185/0.25 | 37.0 | 0 |
|  |  | Propionic | 185/0.5 | 43.5 | 0 |
|  |  | Propionic | 200/0.25 (1) | 27.0 | 16 |
|  |  | Propionic | 200/0.25 (2) | 37.0 | 1 |
|  |  | Propionic | 200/0.5 | 35.7 | 0 |

Examples 7, 8 and 9 illustrate the preparation and properties of laminates that include continuous chitosan film.

Example 7

A chitosan film (Primex ChitoClear® TM-656), prepared from a standard chitosan salt solution in a manner similar to Example 2 (except that the film was only exposed to NaOH solution for about 2 minutes), was heat laminated (175° C., 10 psig (70 kPa), 10 s) to the polyurethane side of a preformed laminate consisting of a 6.7 oz/yd$^2$ (0.23 kg/m$^2$) nylon-cotton blend (50:50) fabric, a dot-matrix pattern of polyurethane melt adhesive, and a 9 μm thick polyurethane film (Omniflex TX 1540 Transport® Brand Film from Omniflex, Greenfield, Mass., USA). The MVTR of the resulting laminate was 10.7 kg/m$^2$/24 h, and no detectable DMMP permeation was observed after 17 h.

Example 8

A 25 μm thick chitosan film prepared as in Example 7 was heat laminated (160° C., 10 psig (70 kPa), 10 s) to the polyurethane side of preformed laminate 4A [(Nomex® pajamacheck fabric (woven, 3.3 oz/yd², 0.11 kg/m² bonded to monolithic polyurethane (PU) film (9 µm thick) with polyurethane adhesive dots (25% coverage). The 9 µm thick polyurethane film was TX 1540 Transport® Brand Film from Omniflex, Co. (Greenfield, Mass., USA)].

Samples were tested in triplicate for sulfur mustard [S(CH₂CH₂Cl)₂] and the nerve agent Soman for 24 h permeation measurements according to the military TOP-8-2-501 (dual flow) protocol. Total accumulation for mustard was ND ("not detected"), ND, and ND for three replicates, and for Soman, ND, 0.07 µg/cm², and 0.11 µg/cm² for three replicates.

Example 9

Two laminate structures, 9A and 9B, were prepared as follows:

9A: Nomex® pajamacheck fabric (woven, 3.3 oz/yd², 0.11 kg/m²) was bonded to monolithic polyurethane (PU) film (5-10 µm thick) with polyurethane adhesive dots (25% coverage).

9B: Nomex® knit fabric (1.5 oz/yd², 51 g/m²) was bonded to polyurethane (PU) film (5-10 µm thick) with polyurethane adhesive dots (25% coverage).

Chitosan film (30 µm thick) was prepared in a manner similar to Example 7, except a 30 mil (0.75 mm) doctor knife was used to cast the film. A sample of the film was heat laminated (130° C. for 45 s at 125 psig (862 kPa)) between laminate structures 9A and 9B, with the PU film facing the chitosan in each case. These samples, with laminate 9A oriented upwards, were then overlaid with an outer shell of 7.5 oz/yd² (0.25 kg/m²) ripstop polybenzimidazole ("PBI")/para-aramid fiber blend (available from Southern Mills, Inc. under the Gemini trademark).

Samples cut from the resulting structure were submitted for sulfur mustard [S(CH₂CH₂Cl)₂] and the nerve agent Soman permeation measurements under NFPA 1994, 2006 Revision testing protocol. The 1 h accumulated permeation for mustard for three replicates was ND ("not detected"), ND, 0.045, (µ/cm²) and for Soman for two replicates, 0.018 and 0.090 (µg/cm²), all passing the NFPA 1994, 2006 Revision requirements of <4.0 µg/cm² one hour cumulative permeation for mustard and <1.25 µg/cm² for Soman.

The following three Comparative Examples show that treatment of a woven fabric in a manner that does not produce a continuous film does not provide a material with satisfactory protection characteristics, as indicated by the DMMP permeation values.

Comparative Example A

A 4.3% aqueous chitosan solution (as the formate) made using a chitosan having a Brookfield viscosity (1% solution in 1% acetic acid) of 20-200 cP (0.02-0.2 Pa·s), obtained from Aldrich Chemical Company (Milwaukee, Wis., USA catalog number 44,886-9), was cast onto a glass plate. A section of Nomex® knitted fabric (E. I. du Pont de Nemours and Company, Wilmington, Del., USA) was laid on the surface of the wet casting. The casting solution wet the Nomex® fabric. The assembly was dried at 100° C., and then soaked in 10% aqueous NaOH for 30 minutes, washed free of base with H₂O, and dried. The treated fabric was found to be liquid water permeable, indicating that a continuous chitosan film had not been produced. Measurements with a NYCO overlayer were MVTR, 21.4 kg/m²/24 h and DMMP permeation, 198 µg in 17 h.

Comparative Example B

In a manner similar to Comparative Example A, a cotton cheese cloth was treated with the chitosan formate solution. The treated cheese cloth was liquid water permeable, indicating a continuous chitosan film had not been produced. Measurements with a NYCO overlayer were MVTR, 18.7 kg/day, DMMP permeation 140 µg in 17 h.

Comparative Example C

A sample of Kevlar®/Nomex® aramid batt thermal liner of the type used in the protective gear of a typical firefighter uniform was obtained from E. I. du Pont de Nemours and Company (Wilmington, Del.). The batt consisted of 75% Kevlar® and 25% Nomex® fibers. The batt was stitched to a face cloth consisting of Nomex®. A piece of the Kevlar®/Nomex® fabric was soaked in water. The wet fabric was passed through a tray containing 2% chitosan (ChitoClear® TM-656) solution in 0.75% aqueous acetic acid, then through nip rolls, which squeezed out the liquid. The treated fabric was then tumble dried at 60° C. for 1 h.

The chitosan-treated, dried fabric was found to be liquid water permeable, indicating that a continuous chitosan film had not been produced. DMMP permeation measured with a NYCO outer shell material was 210 µg DMMP in 17 h, and without a NYCO outer shell material, 305 µg DMMP in 17 h.

Examples 10 through 13 demonstrate the performance of a polyperfluorosulfonic acid ("PFSA") tetrafluoroethylene copolymer film coated with chitosan.

Example 10

A 3" by 3" (7.6 cm by 7.6 cm) piece of Nafion® PFSA 1135 film (E. I. du Pont de Nemours and Company, Wilmington, Del. USA), about 89 microns thick, was swollen in boiling water and then pressed onto a glass plate to make it flat with no bumps or wrinkles. The film was less than 5 mils (0.13 mm) thick. A 4" (10 cm) wide doctor knife with a clearance of 20 mils (0.51 mm), with the side ridges resting on the glass, not on the Nafion® film, was used to coat the Nafion® film with a 6% chitosan (Primex ChitoClear® TM-656, as the formate) aqueous solution. The resulting composite film was dried at 100° C. and remained attached to the glass; a section was subsequently removed via a 3-min treatment with 10% aqueous NaOH solution followed by washing free of base and drying. Using a NYCO overlayer, measurements were made on the untreated Nafion® film, 10A, and the chitosan treated film, 10B and the results are shown below.

A second film was produced in a similar manner and a section of the dried film was then heated at 170° C., resulting in a stiff, very pale yellow film. Using a Nomex® overlayer, MVTR and DMMP permeation measurements were made on the unheated film, 10C, and the heated film, 10D, and the results were shown in Table 3.

TABLE 3

| Sample | Overlayer | Chitosan coated | Heated at 170° C. | MVTR (kg/m²/24 h) | DMMP (µg in 17 h) |
|---|---|---|---|---|---|
| 10A | NYCO | no | no | 27.2 | 42 |
| 10B | NYCO | yes | no | 22.8 | 0 |
| 10C | Nomex | yes | no | 34.5 | 0 |
| 10D | Nomex | yes | yes | 34.5 | 1 |

Example 11

A solution of 5.1 g chitosan (Primex ChitoClear® TM-656) in 93.2 g distilled water was heated to 70° C. 1.66 g glacial acetic acid was added with vigorous stirring. The solution was stored overnight to allow bubbles to dissipate. Calculated chitosan content: 5.1 wt %.

Film 11A was prepared by casting this solution onto 7 mil (0.18 mm) Mylar® polyester film using a 30 mil (0.76 mm) doctor knife. After drying overnight at room temperature, the film (0.7 mil (0.18 mm) thick) was removed from the Mylar® polyester film by lifting an edge with tape. The film sample was found to be insoluble in water. Measurements using a Nomex® overlayer were MVTR, 38.0 kg/m$^2$/24 h and DMMP permeation, 0 µg in 17 h.

Film 11B was prepared by casting the solution onto 0.75 mil (19 µm) Nafion® PFSA film (on Mylar® polyester film backing) using an 8 mil (0.20 mm) (doctor knife. The film was allowed to dry overnight at room temperature. The resulting 0.3 mil (8 µm) chitosan/0.75 mil (19 µm) Nafion® PFSA film was removed from the Mylar® polyester film using tape to lift an edge. Permeation values using a Nomex® overlayer were MVTR, 42.6 kg/m$^2$/24 h and DMMP permeation, 0 µg in 17 h.

Example 12

Chitosan films, 25" (0.64 m) width, 0.2-0.6 mil (5 µm-15 µm) thick, were prepared on a 3 mil (76 µm) Mylar® polyester film base using a modified Worldwide Magnetic Tape Ram slot die coater. A 1.6% aqueous acetic acid solution containing 4.2% chitosan by weight (Primex ChitoClear® TM-656), pre-filtered through 10 µm filters, was charged into a pump cart assembly fitted with two 40 µm filters. Solution was purged through the die to remove any entrained air from the system prior to coating. The chitosan solution was cast onto the Mylar® polyester film base and passed through three heated zones to produce the film. A polyethylene coversheet was added during the film uptake to protect the film surface. To cast a 0.4 mil (10 µm) film the following conditions were used:

Casting Conditions
Line speed: 10 fpm (0.05 m/s)
Pump speed (solution): 55 rpm (5.8 rad/s)
Die-to-web gap: 6 mil (150 µm)
Die vacuum: 1.2 in H$_2$O (299 Pa)
Drying Conditions
Zone 1: 160° F. (71° C.)
Zone 2: 160° F. (71° C.)
Zone 3: 260° F. (127° C.)

The resulting chitosan film had a smooth surface with uniform thickness. Different chitosan film thicknesses were produce by varying the pump speed. The die vacuum was adjusted as needed to stabilize the cast film. The Mylar® polyester film backing and polyethylene coversheet were subsequently removed and permeation values, using a Nomex® overlayer, were determined to be MVTR, 40.0 kg/m$^2$/24 h and DMMP permeation, 4 µg in 17 h.

Chitosan films were also produced from a 1% aqueous formic acid solution containing 5% chitosan by weight (Primex ChitoClear® TM-656) using similar conditions.

Example 13

Films, 25" (0.64 m) width, 1.2-1.4 mil (30 µm-36 µm) thick, were prepared by casting 0.6% aqueous acetic acid solution containing 4.2% chitosan by weight (Primex ChitoClear®-656), pre-filtered through 10 µm filters, onto a Nafion® PFSA substrate with a modified Worldwide Magnetic Tape Ram slot die coater using the process described in Example 12. Chitosan films were cast onto commercial 1.0 mil (25 µm) Gen 1 and Gen 2 CS Nafion® films available from E. I. du Pont de Nemours and Company (Wilmington, Del., USA). The resulting chitosan/Nafion® films demonstrated good thickness uniformity with a smooth, even surface. Permeation values using a Nomex® overlayer were MVTR, 38.6 kg/m$^2$/24 h and DMMP permeation, 0 µg in 17 h.

Examples 14 through 17 illustrate the preparation and performance of laminates containing continuous chitosan film and Nafion® PFSA film.

Example 14

Nafion® PFSA film with a 20 µm dry film thickness supported by 75 µm PET film was obtained from E. I. du Pont de Nemours and Company (Wilmington, Del., USA). A doctor blade with a 0.2 mm gap was used to coat a 5% aqueous solution of chitosan as the formate onto the Nafion® film side while supported by the PET film. This was dried at 150° C. for 2 minutes, and the dry film thickness of the chitosan was 8 µm. The PET was removed, and this chitosan/Nafion® structure was laminated to the polyurethane side of a preformed laminate [Nylon tricot fabric (1.3 oz/yd$^2$, 44 g/m$^2$), bonded to polyurethane film (5-10 µm thick) with polyurethane adhesive dots (25% coverage)], at 160° C., 10 psig (70 kPa), for a total time of 10 s, to produce the final laminate: Nylon tricot/adhesive dots/PU film/chitosan/Nafion®.

Samples of the final laminate were tested in triplicate for 24 h permeation of sulfur mustard [S(CH$_2$CH$_2$Cl)$_2$] and of the nerve agent Soman according to the military TOP-8-2-501 (dual flow) protocol. Total accumulation for mustard was 23.4, 5.8, 15.4 µg/cm$^2$ for three replicates, and for Soman, 1.6, 1.6 µg/cm$^2$, and 2.3 µg/cm$^2$ for three replicates.

Example 15

Nafion® PFSA film with a 20 µm dry film thickness supported by 75 µm PET film was obtained from E. I. du Pont de Nemours and Company (Wilmington, Del., USA). A doctor blade with a 0.2 mm gap was used to coat a 5% aqueous solution of chitosan as the formate onto the Nafion® side while supported by the PET film. This was dried at 150° C. for 2 minutes, and the dry film thickness of the chitosan was 8 µm. This chitosan/Nafion® structure was then laminated to the polyurethane side of a preformed laminate [Nylon tricot fabric (1.3 oz/yd$^2$, 44 g/m$^2$), bonded to polyurethane film (5-10 µm thick) with polyurethane adhesive dots (25% coverage)] at 190° C., 10 psig (70 kPa), for a total time of 10 s. The PET was removed, and the Nafion® side of the structure was then laminated to the polyurethane side of another layer of the preformed laminate at 170° C., 10 psig (70 kPa), for a total time of 10 s., to produce the final laminate: Nylon tricot/adhesive dots/PU film/chitosan/Nafion®/PU film/adhesive dots/Nylon tricot.

Samples of the final laminate were tested in triplicate for 24 h permeation of sulfur mustard [S(CH$_2$CH$_2$Cl)$_2$] and of the nerve agent Soman according to the military TOP-8-2-501 (dual flow) protocol. Total accumulation for mustard is 7.7, 4.7, and 4.7 µg/cm$^2$ for three replicates, and for Soman, ND, ND, and ND µg/cm$^2$ for three replicates.

Example 16

Nafion® PFSA film with a 20 µm dry film thickness supported by 75 µm PET film was obtained from E. I. du Pont de Nemours and Company (Wilmington, Del., USA). A doctor blade with a 0.2 mm gap was used to coat a 5% aqueous solution of chitosan as the formate onto the Nafion® side while supported by the PET film. This was dried at 150° C. for 2 minutes, and the dry film thickness of the chitosan was 8 µm. This chitosan/Nafion® structure was bonded at 190° C. to a 9 µm thick PU film. This PU/chitosan/Nafion®/PET structure was then laminated to the PU side of the preformed prelaminate [Nylon tricot fabric (1.3 oz/yd$^2$, 44 g/m$^2$), bonded to polyurethane (PU) film (5-10 µm thick) with polyurethane adhesive dots (25% coverage)] at 190° C., 10 psig (70 kPa), for a total time of 10 s. The PET was removed, and Nafion side of the structure above was laminated to the PU side of another layer of the preformed prelaminate at 170° C., 10 psig (70 kPa), for a total time of 10 s, to produce the final laminate: Nylon tricot/adhesive dots/PU film/PU film/chitosan/Nafion®/PU film/adhesive dots/Nylon tricot The final laminate was then treated with 3 wash/dry laundry cycles without delamination. The laundered sample was tested in triplicate for 24 h permeation of sulfur mustard $[S(CH_2CH_2Cl)_2]$ and of the nerve agent Soman according to the military TOP-8-2-501 (dual flow) protocol. Total accumulation for mustard was ND, 1.8, and 3.6 µg/cm$^2$ for three replicates, and for Soman, ND, ND, and ND µg/cm$^2$ for three replicates.

Example 17

A chitosan/Nafion® PFSA structure prepared according to Example 13 was bonded to Nomex® fabric (woven, 5.6 oz/yd$^2$, 0.19 kg/m$^2$) with polyurethane adhesive dots (25% coverage). The PET support film on the Nafion® was then removed and the Nafion® side of the structure bonded to Nomex® Jersey fabric (1.3 oz/yd$^2$, 44 g/m$^2$) with polyurethane adhesive dots (25% coverage) to produce the final laminate: Nomex® fabric (woven)/adhesive dots/chitosan/Nafion®/adhesive dots/Nomex® Jersey fabric. The laminate was then baked at 160° C. in air for 2 minutes. MVTR was 30 kg/m$^2$/24 h and DMMP permeation was 2 µg in 17 h.

Examples 18 and 19 illustrate chemical crosslinking of chitosan films after film formation.

Example 18

A chitosan film was prepared in a manner similar to Example 7. While still on the glass, it was painted with a crosslinking fire-proofing solution prepared as follows:

To a solution of 0.8 g Na$_2$HPO$_4$ in 10.5 g distilled water was added 7.2 g of an 80% solution of tetrakis(hydroxymethyl) phosphonium chloride (obtained from Sigma-Aldrich, St. Louis, Mo., USA), (HOCH$_2$)$_4$PCl, followed by 1.68 g urea. [Reference: Donaldson, Normand, Drake, and Reeves, *J. Coated Fabrics*, 3, 250-6 (1974)].

The coated chitosan film was dried at 80° C. and heated at 160° C. for 2 minutes, then allowed to cool. The cooled film was dampened with a damp paper towel to allow it to release from the glass plate, air-dried (ambient conditions). After re-drying, the colorless film was exposed to the flame of a match. The chitosan did not burn or smolder though it did char.

Measurements using a NYCO overlayer were MVTR 10.5 kg/m$^2$/24 h and DMMP permeation 4 µg in 17 h.

Example 19

Primex ChitoClear®TM-656 chitosan powder (7 g) was added to 0.1 N HCl (200 mL) with vigorous stirring. The mixture was heated to 80° C. for 0.5 h. 12.1 N HCl (0.120 mL) was then added. The mixture was stirred at room temperature until all solids had dissolved (1 h). The solution was cast onto a glass plate using a 50-mil (1.3 mm) blade and allowed to dry for 24 hours under ambient conditions. While still on the glass, the film was treated with 10% aqueous sodium hydroxide solution for 2 minutes, rinsed with deionized water, and dried for 2 hours. The film was then treated with 0.1% glutaraldehyde in water for 1 minute, rinsed with deionized water, and dried for 2 hours. The dried film was removed from the glass. Measurements using a Nomex® overlayer were MVTR=21.6 kg/m$^2$/24 h, DMMP permeation=0 µg in 17 h.

Examples 20 through 23 demonstrate the performance of films prepared from chitosan solutions containing reactive chemical additives.

Example 20

To a suspension of 1 g chitosan (Primex ChitoClear® TM-656) in 16 g H$_2$O was added 0.71 g levulinic acid. The resulting viscous solution had small bubbles. Heating in a boiling water bath lowered the solution viscosity and allowed the bubbles to rise rapidly out of the solution. A chitosan film was produced by casting with a 20-mil (0.51 mm) doctor knife onto a glass plate. The film was treated with 10% aqueous NaOH solution and partly dried at 70° C. The moist film was strong and surprisingly elastic. It stretched without tearing when a finger was pressed into it. When dry, the film was stronger than previously prepared chitosan films (e.g., Example 2 film).

Another solution was prepared as above, but using four times the above amounts. After the cast film was dried (at about 90° C.), the film was stiff and clear. After it was allowed to pick up moisture from the ambient atmosphere, it became elastic. After subsequent treatment with 10% aqueous NaOH solution, the film was strong and clear. Films of two thicknesses were prepared, 0.7 mil (18 microns) prepared with a 20-mil (0.51 mm) doctor knife, and 0.4 mil (10 microns) prepared with a 10-mil (0.25 mm) doctor knife and stored at 100% relative humidity. After several hours, the films had absorbed enough moisture to become elastic and still strong.

MVTR and DMMP permeation were determined for the samples using a Nomex® overlayer, as shown in Table 4.

TABLE 4

| Description | MVTR (kg/m$^2$/24 h) | DMMP (µg in 17 h) |
|---|---|---|
| Chitosan/levulinic acid | 25.6 | 0 |
| Chitosan/levulinic acid, 2$^{nd}$ trial, 0.7 mil | 27.0 | 6 |
| Chitosan/levulinic acid, 3$^{rd}$ trial, 0.4 mil | 33.3 | 8 |

Example 21

21A. To a suspension of 3 g Primex ChitoClear® TM-656 chitosan (18 mmol —NH$_2$) in 30 mL H$_2$O was added a solution consisting of 0.55 g (12 mmol) formic acid, 0.44 g (6 mmol) 50% glyoxylic acid in H$_2$O, and 20 mL H$_2$O. The solution was rolled on a roll mill until uniform. After the bubbles had risen out of the solution, films were cast on glass plates using a 25-mil (0.64 mm) doctor knife. The films were dried at 100° C., treated with 10% aqueous NaOH solution for 1 minute, dried, removed from the glass plate, and tested. When wet with H$_2$O, the film was strong and slightly elastomeric.

21B. To 33 g of a 6% solution of Primex ChitoClear® TM-656 chitosan (12 mmol —$NH_2$) as the formate were added 0.15 g (4 mmol) glyoxylic acid (as 0.3 g of 50% glyoxylic acid in $H_2O$). Chitosan film was prepared from this solution as in 12A. The film was elastomeric when wet. MVTR and DMMP permeation measurements were made using a Nomex® overlayer and are presented in Table 5.

TABLE 5

| Sample | MVTR (kg/m$^2$/24 h) | DMMP (μg in 17 h) |
|---|---|---|
| 21A | 34.5 | 0 |
| 21B | 31.3 | 0 |

Example 22

A few drops of 10% tetrakis(hydroxymethyl)phosphonium chloride ("TK") aqueous solution were added to a 5% aqueous solution of Primex ChitoClear® TM-656 chitosan (as the formate). A gel formed in 1 min at room temperature, suggesting the chitosan had undergone crosslinking. At 0° C., gel formation took 6 min, and there was very little change in viscosity in the first 3 min.

22A. To 10 g of a 5% aqueous solution of Primex ChitoClear® TM-656 chitosan (as the formate) (3 mmol —$NH_2$ groups) was added 0.35 g isopropyl alcohol and 65 mg of 10% TK aqueous solution (0.03 mmol).

22B. same as 22A, except for using 0.3 g 10% TK aqueous solution (0.66 mol).

The 22A and 22B solutions were each cast onto glass plate using a 40-mil (1.0 mm) doctor knife and dried at 100° C. To release the films from the glass, they were covered with a damp paper towel. MVTR and DMMP permeation were measured with a NYCO overlayer. Results are presented in Table 6.

TABLE 6

| Sample | MVTR (kg/m$^2$/24 h) | DMMP (μg in 17 h) |
|---|---|---|
| 22A | 21.3 | 0 |
| 22B | 21.3 | 0 |

Example 23

0.12 g. Aliquat 336 (N-methyl-N,N-dioctyl-1-octanaminium chloride, a liquid) (5% by weight in the final film was added to 80 g of a 5% aqueous solution of Primex ChitoClear® TM-656 chitosan (as the formate). Aliquat 336 is a mixture of quaternary amine salts having large alkyl groups. The film obtained by making a 40 mil (1.0 mm) casting on a glass plate, and drying at 100° C., released from the glass spontaneously. It was treated with 10% aqueous NaOH solution, washed free of base with water, remounted on a glass plate and dried at about 70° C. The resulting film was elastic when wet and strong when dry. MVTR was 20 kg/m$^2$124 h, DMMP permeation was 1 μg in 17 h.

Examples 24, 25 and 26 demonstrate the effect of sugars on chitosan film performance.

Example 24

Into 50 g 6% chitosan (Primex ChitoClear® TM-656) as the formate salt in water (3 g, 19 mmol) was dissolved 0.17 g (1 mmol) glucose, producing a clear solution. The solution was cast onto a glass plate using a 20-mil (0.51 mm) doctor knife. The plate/casting assemblage was placed on an open press platten at 104° C. for 4 min, the time necessary to dry the casting. The film was then treated with 10% aqueous NaOH solution for 2 min at room temperature, washed free of base, and, while in a water bath, floated onto a glass plate, smoothed, and dried at about 70° C. Additional films were then wrapped in aluminum foil and heated for either 2 or 5 minutes at 104° C. MVTR and DMMP, measurements for these samples and a chitosan film control are presented in Table 7. Films were qualitatively strong.

TABLE 7

|  | Chitosan | Chitosan/Glucose |
|---|---|---|
| Time at 104° C. (minutes) | 0 | 0 |
| MVTR (kg/m$^2$/24 h) | 28.6 | 29.8 |
| DMMP (μg in 17 h) | 0 | 0 |

Example 25

A solution consisting of 42 g water, 0.92 g (20 mmol) formic acid and 0.7 g (2 mmol) sucrose was heated in a closed bottle in a boiling water bath to convert at least part of the sucrose to fructose and glucose. To the cooled solution was added 3 g. (20 mmol —NH2 group) chitosan (Primex ChitoClear® TM-656). The mixture gelled immediately. The container was shaken vigorously then placed on roll mill until the chitosan had dissolved. The solution was pressure filtered through coarse filter paper.

Films were cast onto glass plates and dried on a 108° C. press platen for 5 minutes. The film was treated with 10% NaOH aqueous solution for 2 minutes, washed free of base and dried. The film was then heated at 104° C. for 15 minutes and washed with water to remove unreacted sugars. MVTR and DMMP, measurements are presented in Table 8 along with data for a chitosan film control.

TABLE 8

|  | Chitosan/Sucrose | Chitosan |
|---|---|---|
| MVTR (kg/m$^2$/24 h) | 25.6 | 28.6 |
| DMMP (μg in 17 h) | 6 | 0 |

Examples 26 through 30 illustrate that chitosan may be blended with other polymers, soluble and insoluble and such blends exhibit high MVTR and low stimulant permeation.

Example 26

Approximately 0.3 g Primex ChitoClear® TM-656 chitosan and 0.3 g nylon 4,6 (Aldrich Chemical Company, Milwaukee, Wis., USA) were dissolved in 12 mL formic acid. To promote dissolution, the mixture was heated to 90° C., then rolled on a roll mill repeatedly until a uniformly cloudy solution resulted. A film was prepared by casting onto a glass plate and drying. Treatment with 10% aqueous NaOH for about 2 minutes resulted in a clear, tough film. The dry films increased 8% in weight by absorption of water from the atmosphere upon standing overnight.

A nylon 4,6 film (30 μm thickness) was prepared by dissolving the nylon in formic acid, then casting onto a glass plate. A solution of chitosan/nylon 4,6 was prepared by dissolving 3.75 g chitosan (Primex ChitoClear® TM-656) and 1.25 g nylon 4,6 in 60 g formic acid. Films of the chitosan/nylon 4,6 blend were cast using a 20-mil (0.51 mm) doctor knife and a 10-mil (0.25 mm) doctor knife, which produced 1-mil (25 microns) and 0.5-mil (13 microns) thick films, respectively.

Results of MVTR ($kg/m^2/24$ h) and DMMP (µg in 17 h) permeation measurements on the films are shown in Table 9.

TABLE 9

| Sample Description | MVTR ($kg/m^2/24$ h) | DMMP (µg in 17 h) |
|---|---|---|
| Nylon 4,6 film | 3.2 | 78 |
| 3:1 chitosan: nylon 4,6 (25 micron) | 11.4 | 11 |
| 3:1 chitosan: nylon 4,6 (13 micron) | 18.2 | 17 |

Example 27

A chitosan solution prepared according to the standard method was mixed with Permax™ 200 polyurethane dispersion (an aqueous dispersion manufactured by Noveon, Inc., a subsidiary of The Lubrizol Corporation, Wickliffe, Ohio, USA) with an 85/15 chitosan/polyurethane weight ratio in terms of dry solids. The chitosan/polyurethane blend was cast, dried, NaOH quenched, and then dried again. DMMP permeation of the 25 µm thick film was found to be 3 µg after 17 h.

Example 28

In a manner similar to Example 27, a film of chitosan/polyurethane with a 30/70 weight ratio in terms of dry solids was prepared. The 20 µm thick chitosan/polyurethane blend film was heat laminated (165° C.) to a preformed laminate [6.7 oz/yd² NYCO fabric (0.23 $kg/m^2$) bonded to Pebax® film (6 µm thick) with polyurethane adhesive dots (25% coverage)]. MVTR of the laminate was 15 $kg/m^2$/day and acrylonitrile permeation was 10 µg in 1 h.

Example 29

A mixture of 50 g of a 5% aqueous solution of Primex ChitoClear® TM-656 chitosan (as the formate) and 0.83 g powdered cellulose (Aldrich Chemical Company, 20 micron screen) was rolled on a mill until the dispersion was visually uniform, then placed under vacuum to remove bubbles. The dispersion was cast onto a glass plate using a 25-mil (0.64 mm) doctor knife, dried at 100° C., treated with 10% NaOH aqueous solution, washed with water and dried (Sample 29A). A second film was made similarly, except after drying it was then enclosed in aluminum foil and heated at 150° C. for 5 min, then treated with 10% NaOH aqueous solution, washed with water and dried (Sample 29B) MVTR and DMMP measurements are presented in Table 10.

TABLE 10

| Sample | MVTR ($kg/m^2/24$ h) | DMMP (µg in 17 h) |
|---|---|---|
| 29A | 22.2 | 0 |
| 29B | 27.0 | 0 |

Example 30

To 80 g of a 5% aqueous solution of Primex ChitoClear® TM-656 chitosan (as the formate) was added 1 g ARGO® Corn Starch. The mixture was ball milled to disperse the cornstarch. One portion of the dispersion was cast onto a glass plate, dried at 100° C., treated with 10% NaOH aqueous solution, washed with water and dried to form a cloudy, 0.9 mil (23 microns) thick film (Sample 30A). A second portion of the dispersion was heated for 2 h at 100° C., and then converted into a film as in 30A. The resulting film (Sample 30B) was 0.8 mil (20 microns) thick and clear. The MVTR of each film was 20.8 $kg/m^2/24$ h. DMMP permeation was 3 µg in 17 h for Sample 30A, 1 µg in 17 h for Sample 30B.

Examples 31, 32 and 33 show that small amounts of inorganic fillers may be added to the chitosan film without negatively impacting the MVTR or DMMP barrier properties.

Example 31

A dispersion of 30 mg sepiolite (hydrous magnesium silicate; Pangel® S9, Grupo Tolsa, Madrid, Spain) in 2 mL water was added to 33 g of a 6% chitosan (Primex ChitoClear® TM-656) solution as the formate salt in water (2 g chitosan/0.55 g formic acid). The mixture in a bottle was rolled on a mill until it was uniform. The product was cast onto a clean glass plate with a 20-mil (0.51 mm) doctor knife. After drying at 100° C., the film was treated with 10% NaOH/water for 10 minutes. The dried film contains 1.5% sepiolite. MVTR and DMMP permeation measurements are presented in Table 11.

Example 32

The procedure for Example 31 was followed to make the solution, except, in place of the sepiolite, 0.11 g Cloisite® Na+ (montmorillonite, Southern Clay Products, Inc., Gonzales, Tex., USA) was added to give a dried film with 5.5% mineral. In addition, the film was cast with a 20-mil (0.51 mm) doctor knife onto a piece of Mylar® polyester sheet that had been taped onto an aluminum plate. The Mylar® had first been cleaned with methanol. The assemblage was heated at 90° C. in an oven with a slight vacuum for 20 minutes. After drying, it was treated with 7% NaOH/water for 15 minutes, rinsed with tap water for 4 minutes, and dried overnight under vacuum and nitrogen. MVTR and DMMP permeation measurements are presented in Table 11.

Example 33

The procedure for Example 32 was followed, except, in place of the sepiolite, 0.11 g Scotchlite™ Glass Bubbles S60/18000 (3M, Minneapolis, Minn., USA) was added to give a dried film with 5.5% glass bubbles. MVTR and DMMP permeation measurements are presented in Table 11.

TABLE 11

| Example | Filler Type | Weight % Filler | MVTR ($kg/m^2/24$ h) | DMMP (µg in 17 h) |
|---|---|---|---|---|
| 2 | None | 0 | 23.8 | 0 |
| 31 | Pangel ® S9 sepiolite | 1.5 | 31.3 | 0 |
| 32 | Cloisite ® Na+ | 5.5 | 31.3 | 0 |
| 33 | Scotchlite ™ Glass Bubbles S60/18000 | 5.5 | 33.3 | 0 |

Where an apparatus or method is stated or described herein as comprising, including, containing, having, being composed of or being constituted by certain components or steps, it is to be understood, unless the statement or description explicitly provides to the contrary, that one or more components or steps other than those explicitly stated or described may be present in the apparatus or method. Alternatively, an embodiment of an apparatus or method of this invention may be stated or described as consisting essentially of certain components or steps, indicating the absence of components or steps that would materially alter the principle of operation or the distinguishing characteristics of the apparatus or method. Further, if an apparatus or method is stated as consisting of certain components or steps, components or steps other than those as stated or described are not present therein.

Where the indefinite article "a" or "an" is used with respect to a statement or description of the presence of a component in an apparatus, or a step in a method, of this invention, it is to be understood, unless the statement or description explicitly provides to the contrary, that the use of such indefinite article does not limit the presence of the component in the apparatus, or of the step in the method, to one in number.

What is claimed is:

1. A finished article comprising a laminate comprising:
   (a) an insoluble continuous chitosan film,
   (b) a substrate onto which the chitosan film is adhered, and
   (c) at least one layer of fabric, wherein: the continuous chitosan film and a layer of fabric are bonded discontinuously using an adhesive that is present as an array of adhesive dots, in a pattern of lines or in a pattern of curves, the substrate comprises a film comprising a polar polymer or a sheet comprising a polar polymer, wherein the polar polymer is an elastomer, glassy polymer, or semi-crystalline material, and wherein the substrate is incorporated into the laminate, and the fabric is woven or nonwoven and comprises one or more members selected from the group consisting of aramids, polybenzimidazoles, nylons, polyesters, and cotton, said article being chemically protective and selectively permeable to water vapor such that:
   the Moisture Vapor Transport Rate is at least 2 $kg/m^2/24$ h,
   the transport rate is <4.0 $\mu g/cm^2$ one hour cumulative permeation for mustard, and
   the transport rate is <1.25 $\mu g/cm^2$ one hour cumulative permeation for Soman, wherein the finished article is selected from the group consisting of:
   items of apparel selected from the group consisting of coveralls, protective suits, coats, jackets, raingear, ski pants, gloves, socks, boots, shoe covers, boot covers, trousers, hoods, hats, masks, and shirts; shelters; and protective covers.

2. The finished article according to claim 1 wherein the chitosan film further comprises one or more members selected from the group consisting of natural polymers, synthetic polymers, crosslinking agents, fillers, flame retardants, plasticizers, tougheners, and stabilizers, and wherein the film comprises at least 50% chitosan by weight.

3. The finished article according to claim 1 wherein the substrate is essentially without protrusions above the plane of the substrate that are higher than the desired thickness of a coating of chitosan solution that will be transformed into the chitosan film.

4. The finished article according to claim 1 wherein the polar polymer is selected from the group consisting of perfluorosulfonic acid tetrafluoroethylene copolymers, polyurethanes, polyether block polyamide copolymers, polyether block polyester copolymers, sulfonated styrene-polyolefin di- and tri-block copolymers, and polyvinyl alcohol homopolymers and copolymers.

5. The finished article according to claim 1 comprising an outer shell, and optionally an inner liner, each independently comprising at least one member of the group consisting of woven fabric and nonwoven fabric.

6. The finished article according to claim 5 wherein the woven or nonwoven fabric comprises one or more members selected from the group consisting of aramid, polybenzimidazole, nylon, polyesters, and cotton.

7. The finished article according to claim 1 further comprising at least one additional layer.

* * * * *